(12) United States Patent
Carone et al.

(10) Patent No.: US 12,124,294 B2
(45) Date of Patent: Oct. 22, 2024

(54) ADJUSTABLE TEXTILES

(71) Applicant: Alarm.com Incorporated, Tysons, VA (US)

(72) Inventors: Johnathan Michael Carone, McLean, VA (US); Isaac Murakami, Fairfax, VA (US); Matthew Daniel Correnti, Newtown Square, PA (US); Eric Liao, Fairfax, VA (US); Alice Kuprenas, Fairfax, VA (US); Alexander Prugh, Wasington, DC (US)

(73) Assignee: Alarm.com Incorporated, Tysons, VA (US)

( * ) Notice: Subject to any disclaimer, the term of this patent is extended or adjusted under 35 U.S.C. 154(b) by 964 days.

(21) Appl. No.: 17/140,935

(22) Filed: Jan. 4, 2021

(65) Prior Publication Data

US 2021/0208625 A1    Jul. 8, 2021

Related U.S. Application Data

(60) Provisional application No. 62/958,004, filed on Jan. 7, 2020.

(51) Int. Cl.
| | |
|---|---|
| *G06F 1/16* | (2006.01) |
| *A61B 5/00* | (2006.01) |
| *G06F 16/9035* | (2019.01) |
| *G06N 20/00* | (2019.01) |
| *A47G 9/02* | (2006.01) |

(52) U.S. Cl.
CPC ............ *G06F 1/163* (2013.01); *A61B 5/0008* (2013.01); *G06F 16/9035* (2019.01); *G06N 20/00* (2019.01); *A47G 9/023* (2013.01)

(58) Field of Classification Search
CPC ... G06F 1/163; G06F 16/9035; A61B 5/0008; A61B 5/02438; A61B 5/1118; A61B 5/6891; A61B 5/01; A61B 5/4812; G06N 20/00; A47G 9/023
USPC ......................................................... 700/299
See application file for complete search history.

(56) References Cited

U.S. PATENT DOCUMENTS

| | | | |
|---|---|---|---|
| 2014/0277308 A1* | 9/2014 | Cronise ..................... | A61F 7/00 607/112 |
| 2019/0099009 A1* | 4/2019 | Connor ................... | A61B 5/398 |
| 2022/0273052 A1* | 9/2022 | Nidam ................. | A41D 31/065 |

FOREIGN PATENT DOCUMENTS

| | | |
|---|---|---|
| CN | 101292781 B | * 10/2010 |
| DE | 102015226237 A1 | * 6/2017 |

* cited by examiner

*Primary Examiner* — Chun Cao
*Assistant Examiner* — Michael Tang
(74) *Attorney, Agent, or Firm* — Fish & Richardson P.C.

(57) ABSTRACT

Methods, systems, and apparatus, including computer programs encoded on a computer storage medium, for adjusting an adjustable textile based on sensor data. The methods, systems, and apparatus include actions of receiving sensor data from one or more sensors installed at a property, generating an analysis result by analyzing the sensor data, and determining, based on the analysis result, an action that adjusts an inflation level of an adjustable textile at the property.

20 Claims, 5 Drawing Sheets

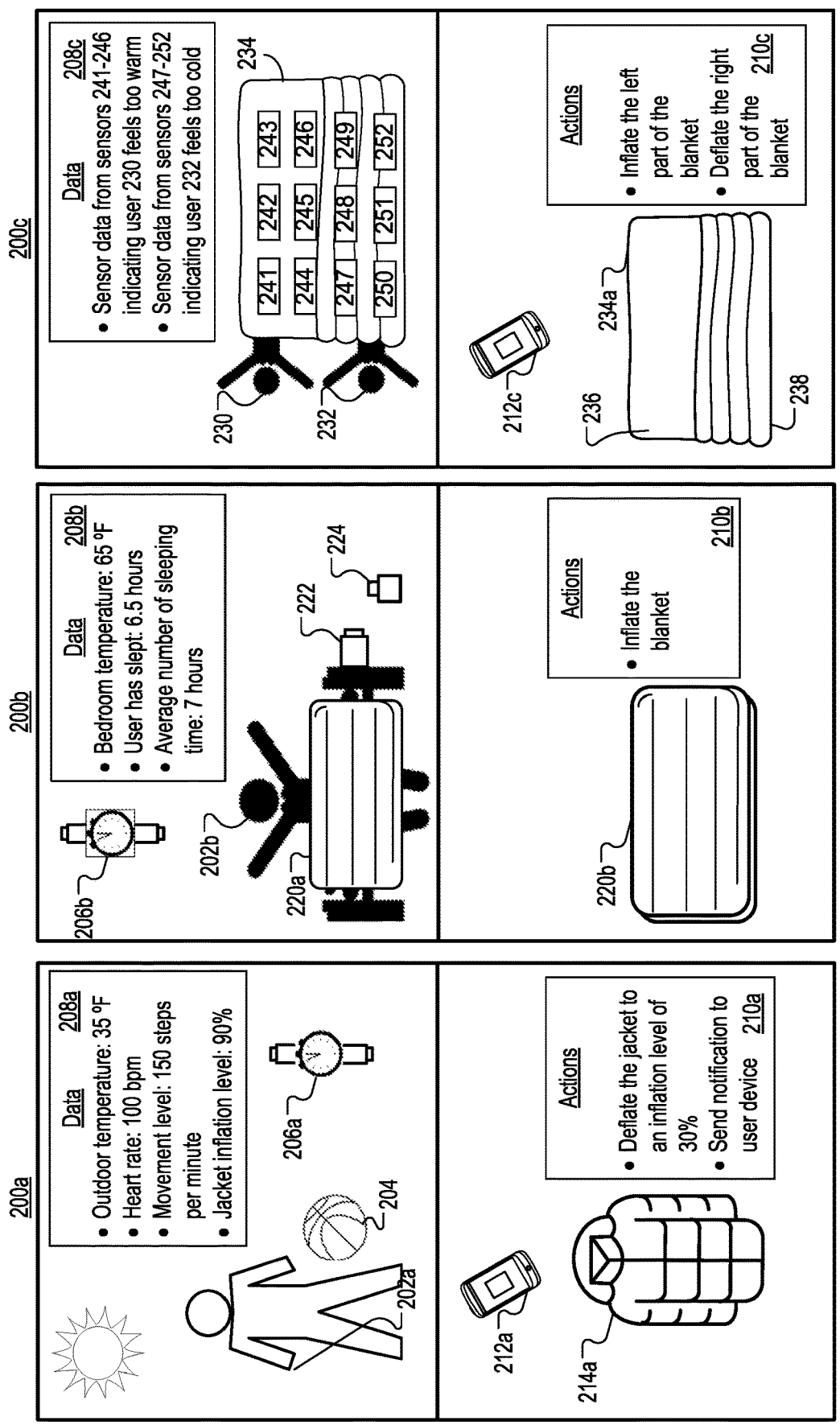

ADJUSTABLE TEXTILES

CROSS-REFERENCE TO RELATED APPLICATIONS

This application claims the benefit of U.S. Provisional Application Ser. No. 62/958,004, filed Jan. 7, 2020, which is incorporated by reference in its entirety.

TECHNICAL FIELD

This disclosure application relates generally to adjustable textiles.

BACKGROUND

Humans naturally have fluctuating body temperatures that vary throughout different times of the day. Humans also face various levels of environmental temperatures, e.g., seasonal or regional changes. When the natural body temperatures are not met, discomfort occurs. To overcome the discomfort, humans adjust layers and types of apparels and textiles, e.g. clothing, sleeping bag or blanket. The need to frequently adjust layers and types of apparels causes not only inconvenience, but also significant cost for purchasing and storing apparels and textiles.

BRIEF DESCRIPTION OF THE DRAWINGS

FIGS. 2A-2C are diagrams illustrating examples of using adjustable textiles in various situations.

Like reference numbers and designations in the various drawings indicate like elements.

DETAILED DESCRIPTION

The disclosed systems, methods, and techniques relate to textiles, e.g., clothing or blanket, that can be configured to adjust their insulation properties based on the surrounding environment and commands from a home security system. Sensors of the home security system may gather sensor data and analyze the sensor data to determine a level of adjustment for the textile. By adjusting the textile's insulation properties, the textile can provide the ability to maintain an individual's body temperature to aid in comfort and can help match the average body temperature cycle that causes body temperature fluctuates through different times of the day.

An adjustable textile can dynamically adjust its insulative capacity by either adding or removing insulation material from the adjustable textile. For example, a blanket can be configured to add or remove air inside the blanket. If the blanket needs to be more insulative, air can be blown into the blanket, allowing the blanket to have more space between the down feathers, and leading to less heat transfer between the body and the room. If the blanket needs to be less insulative, air can be sucked out of the blanket, compacting the down feathers, and leading to greater heat transfer between the body and the room.

Figure 1:
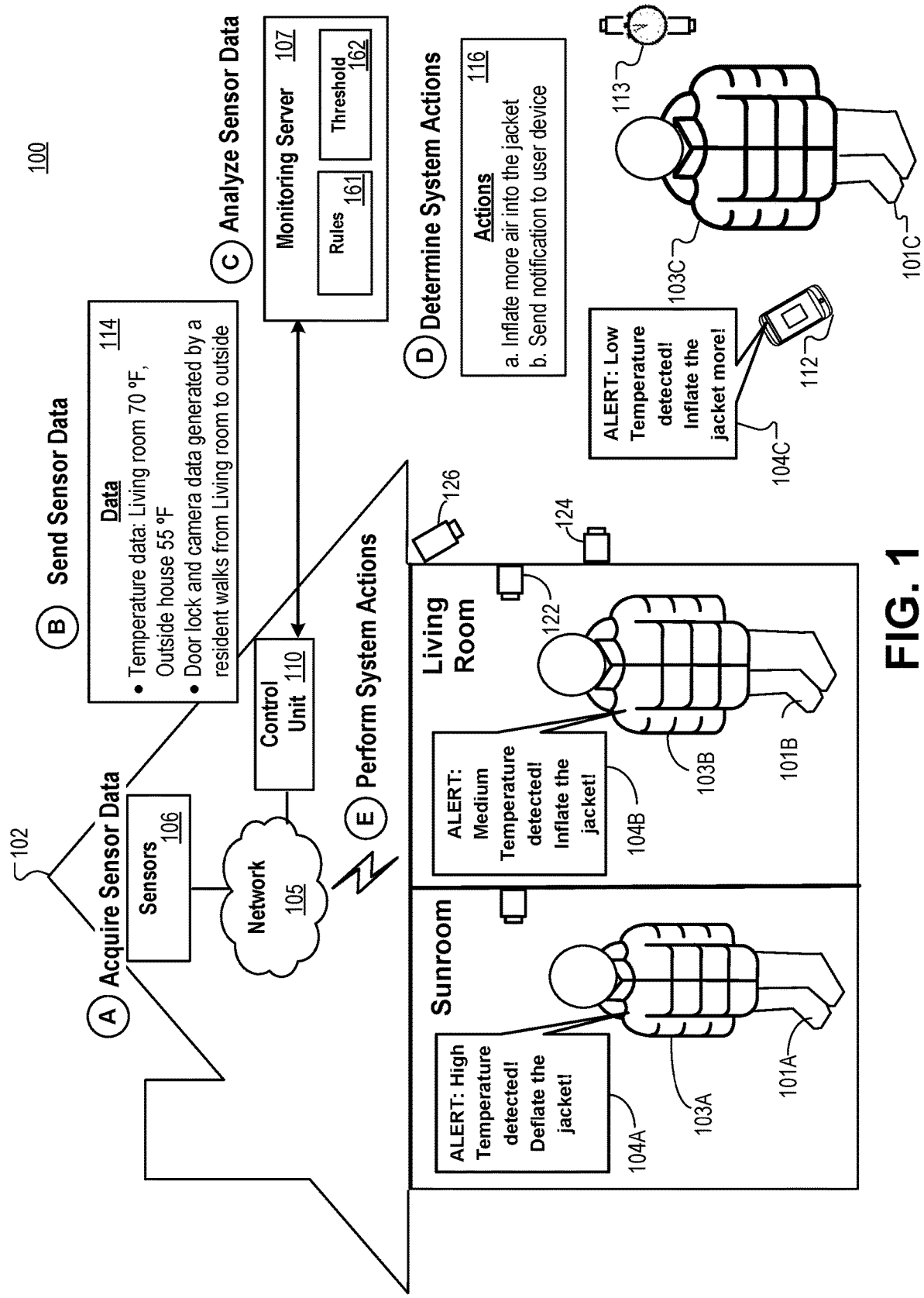
FIG. 1 is a diagram illustrating an example of a monitoring system and a jacket with an adjustable insulative capacity.

FIG. 1 is a diagram illustrating an example of a monitoring system 100 and a jacket 103A with an adjustable insulative capacity. The jacket 103A can be worn by a resident 101A living in a property 102. The system 100 includes a property 102 monitored by one or more sensors 106, e.g., temperature sensors, that can acquire temperature data of the property 102. The system 100 also includes a monitoring server 107 that analyzes the temperature data, and other sensor data to determine one or more insulation configuration actions related to the jacket 103A. The insulation configuration actions can be adding or removing air inside the jacket 103A worn by a resident 101A. FIG. 1 includes stages (A) through (E), which represent a flow of data.

For example, the same resident 101A, 101B, and 101C can move to various locations in and around the property 102, such as the sunroom, the living room and outside. The same jacket 103A, 103B, and 103C can be configured with different levels of insulation according to system actions 104A, 104B, and 104C determined based on temperature data measured by the temperature sensors 120, 122, and 124 in each area of the property 102. When the resident 101B walks from the sunroom to the living room, the jacket 103B can be configured with more insulation because the living room is cooler than the sunroom. When the resident 101C walks from the living room to a cold outdoor environment, the jacket 103C can be configured with even more insulation because the outdoor temperature is even lower than the temperature of the living room.

The system 100 includes an adjustable textile, such as a jacket 103A in FIG. 1. As described above, the adjustable textile can be a clothing, a sleeping bag, or a blanket worn by a resident of the property 102. The adjustable textile can be configured with various levels of insulation to provide a comfortable level of warmth to the resident based on sensor data collected by the sensors 106. For example, a jacket 103A is configured with less insulation, e.g., less air inside the jacket, based on temperature data of a warm sunroom. The same jacket 103B is configured with more insulation, e.g., more air inside the jacket, based on temperature data of a cooler living room. The same jacket 103C is configured with even more insulation, e.g., a maximum amount of air inside the jacket, based on temperature data of a cold outdoor environment near the property 102.

The adjustable textile 103A can include one or more layers of one or more base materials, e.g., one or more layers of down feathers, and one or more insulation materials, e.g., air. The adjustable textile can be configured to adjust the amount of insulation materials in the one or more layers of base materials. For example, the jacket 103C can be a thicker jacket with more insulation by adding more air inside the jacket. The adjustable textile 103A can be configured according to an insulation configuration action 104A. The adjustable textile 103A can add or remove air automatically following the insulation configuration action 104A. Alternatively or in combination, the adjustable textile 103A can be manually inflated or deflated through a manual pump used by a resident 101A wearing the adjustable textile 103A.

In some implementations, the adjustable textile 103A includes one or more temperature sensors on the side that sense the temperature of the body of the user wearing the adjustable textile. Multiple temperature sensors can be used to measure an average temperature of the body. Based on the measured average temperature of the body, the system can determine whether an adjustment needs to be made and air can be added or taken out accordingly.

The sensors 106 in a home security system can collect sensor data. Many residents and homeowners equip their properties with home security systems to enhance the security, safety, or convenience of their properties. The sensors 106 in a home security system can include one or more temperature sensors which acquire temperate data from one or more areas of the property 102. For example, the sensors 120, 122 and 124 can acquire temperature of a sunroom, temperature of a living room and temperature of an outside environment of the property 102. In some implementations, the sensors 106 can include motion detectors that sense movement in an area of the property 102. For example, a motion detector can detect that a resident 101A moved from a sunroom to a living room of the property 102.

The sensors 106 can also include one or more visible light cameras 126 that are in various locations of the property 102. The visible light camera 126 can capture image or video data of the physical surroundings detectable within the camera's field of view. In some implementations, the visible light camera may be paired with one or more motion sensors, where detection of movement by the motion sensor triggers the visible camera to capture image or video data. In some implementations, the visible light camera can include a microphone for capturing audio data detected in the vicinity of the visible light camera. By analyzing the image, video and/or audio, the system 100 can determine a location and/or movement of a resident 101A. The sensors can also include door or window lock sensors, utility or resource usage sensors, microphones, humidity sensors, light sensors, or other sensors. Other possible sensors are described below in FIG. 4.

The one or more sensors 106 communicate with a control unit 110 that is located at the property 102. The control unit 110 can be, for example, a computer system or other electronic device configured to communicate with the sensors 106. The control unit 110 can also perform various management tasks and functions for the system 100. In some implementations, the resident 101A of the property, or another user, can communicate with the control unit 110 (e.g., input data, view settings, or adjust parameters) through a physical connection, such as a touch screen or keypad, through a voice interface, and/or over a network connection.

The sensors 106 may communicate with the control unit 110 over a network 105. The network 105 can be any communication infrastructure that supports the electronic exchange of data between the control unit 110 and the one or more sensors 106. For example, the network 105 may include a local area network (LAN). The network 105 may be any one or combination of wireless or wired networks and may include any one or more of Ethernet, Bluetooth, Bluetooth LE, Z-wave, Zigbee, or Wi-Fi technologies.

The one or more sensors 106 send sensor data 114 to the control unit 110 through the network 105. For example, temperature sensors 120, 122, and 124 can send temperature data to the control unit 110. Similarly, the sensors 106 can send motion sensing data from one or more motion detectors, status data from one or more door or lock sensors (e.g., door open, lock secured), or light level data from one or more light detectors. The sensors 106 can also send image data from one or more visible light cameras 126 (e.g., visible light images and/or video) to the control unit 110.

In stage (A), the one or more sensors 106 of a home security system acquire temperature data 114 of one or more areas of the property 102. In the example of FIG. 1, three temperature sensors 120, 122, and 124 can be separately installed in a sunroom, a living room and outside of the property 102. The temperature sensors are configured to measure temperature of the respective areas of the property 102 constantly or in an interval. In the example of FIG. 1, the temperature sensors 122 and 124 can acquire temperature data 114, which indicates that the current temperature of the living room is 70° F. and the current temperature of the outdoor environment is 55° F. The temperature sensors provide the temperature data to the control unit 110 through the network 105.

Concurrently, other sensors 106 of the home security system may collect sensor data related to the same area of the property 102, or related to another area of the property 102, and send the sensor data to the control unit 110. For example, a door lock sensor may collect data indicating that a door from the living room to the outside is open. This can trigger a camera 126 to capture an image or video of around the door. Additionally or alternatively, a motion detector may detect motion activities from the living room to outside of the house. In some implementations, the sensors 106 can include door or window lock sensors, utility or resource usage sensors, microphones, humidity sensors, light detectors, or other sensors.

The control unit 110 receives the sensor data 114 from the sensors 106. The control unit may also receive or generate other monitoring system data in the home security system, and receive or generate information related to other devices connected to the home security system. For example, the control unit 110 may receive time and date information, a thermostat setting, an appliance setting, etc. In some implementations, the sensor data 114 can include data related to a mobile device 112 of the resident 101C. In some examples, monitoring system data can indicate whether the mobile device 112 is present at the property 102 (e.g., based on whether the device 112 is connected to a Wi-Fi network at the property 102 or whether a GPS signal indicates that the device 112 is at the property 102). In some examples, the control unit 110 can receive data related to body temperature, heart rate, and other physical properties of the resident 101C, measured and sent by a wearable mobile device 113. In some implementations, the control unit 110 can receive data of a current level of inflation of an adjustable textile 103C.

In stage (B), the control unit 110 sends various sensor data 114 to a monitoring server 107, where the sensor data 114 can include the temperature data, and/or other monitoring system data. The monitoring server 107 may be, for example, one or more computer systems, server systems, or other computing devices that are located at the property 102 or remotely from the property 102. The monitoring server 107 is configured to process the sensor data information collected by the sensors 106 at the property 102. In some implementations, the monitoring server 107 is a cloud computing platform.

In some implementations, the control unit 110 communicates with the monitoring server 107 via a long-range data link. The long-range data link can include any combination of wired and wireless data networks. For example, the control unit 110 can exchange information with the monitoring server 107 through a wide-area-network (WAN), a broadband Internet connection, a cellular telephony network, a wireless data network, a cable connection, a digital subscriber line (DSL), a satellite connection, or other electronic means for data transmission. The control unit 110 and the monitoring server 107 may exchange information using any one or more of various communication synchronous or asynchronous protocols, including the 802.11 family of protocols, TCP/IP, GSM, 3G, 4G, 5G, LTE, CDMA-based data exchange or other techniques. In some implementations, the long-range data link between the control unit 110 and the monitoring server 107 is a secure data link (e.g., a virtual private network) such that the data exchanged between the control unit 110 and the monitoring server 107 is encoded to protect against interception by an adverse third party.

In some implementations, various sensors 120 located at the property 102 can communicate directly with the monitoring server 107 (e.g., sending sensor data directly to the monitoring server 107 rather than sending data to the monitoring server 107 via the control unit 110). For example, one or more of the cameras 126, the sensors 120, 122, 124, or other devices at the property 102 can provide some or all of the data 114 to the monitoring server 107, e.g., through an Internet connection.

In some implementations, the control unit 110 processes some or all of the data 114 before sending the data 114 to the monitoring server 107. For example, the control unit 110 may compress or encode the camera image data to reduce the bandwidth required to support data transmission. The control unit 110 can also aggregate, filter, transform, analyze or otherwise process some or all of the data 114.

In the example of FIG. 1, the control unit 110 sends to the monitoring server 107 data 114 that includes the measured temperatures of a living room, measured temperature of an outdoor environment, door lock and camera data indicating that a resident walks from the living room to outside.

In stage (C), the monitoring server 107 analyzes the data 114 received from the control unit 110. The monitoring server 107 may analyze measured temperature data included in data 114 to identify the outside is much colder than the living room. For example, in FIG. 1, the monitoring server 107 may analyze the sensor data and may determine that the surrounding temperature of the resident 101B is going to change from 70° F. to 55° F., resulting in a change of −1° F. in temperature.

The monitoring server 107 may also analyze the door lock and camera data to determine that a resident 101B wearing an adjustable temperature jacket 103B walked from living room to outside. The monitoring server 107 can analyze the data 114 to identify a resident 101B and an adjustable textile 103B in the image or video data by any of various image processing techniques. In some implementations, the monitoring server 107 may perform facial recognition or other processing to identify a particular resident 101B depicted in the image data.

In stage (D), in response to analyzing the data 114, the monitoring server 107 determines one or more system actions 116. The system actions 116 can include adding or removing a certain amount of air inside the jacket 103C. For example, if the temperature of an outside environment is below 20° F., the monitoring server 107 can determine that the inflation percentage of a jacket should be 90%. And if the current inflation percentage of the jacket is 50%, the monitoring server can determine an insulation configuration action to be "increase the inflation level of the jacket by 40%".

The server 160 can include a rules engine, which determines the system actions 116 based on one or more rules 161. The rules 161 can be default rules, set in advance by a system administrator. The rules 161 can also be custom rules, set or modified by the resident 101C or another authorized user of the monitoring system. The rules 161 may be general, such that they are applied to more than one property, or they may be specific to the particular property 102. In some implementations, the rules 161 can be customized according to the particular area of the property 102 (e.g., different rules 161 for different rooms of the property 102), the time of day, or other factors. In some implementations, the rules 161 can be adjusted based on the analyzed data 114.

In some implementations, the rules 161 include one or more thresholds 162, where a threshold 162 can relate to the detected temperature of a particular area in the property 102. The rules 161 can indicate that, under certain circumstances, if the detected temperature of an area of the property 102 is determined to satisfy the threshold 162, the monitoring server 107 should perform one or more system actions 116 related to the adjustable textile 103B. For example, the rules 161 can indicate that if a resident moves from a living room to an outside area with a temperature change greater than a threshold 162 of −5 degrees Fahrenheit, the monitoring server 107 can determine system actions 116, including (a) inflating more air to the jacket 103C and (b) sending a notification to the user device 112 of the resident 101C.

Generally, the resident 101C can customize the one or more rules 161 and thresholds 162 according to his preferences. In some implementations, the resident 101C can set the one or more rules 161 and/or thresholds 162 through a software application executing on his mobile device 112, through a graphical interface provided by a browser or application on a computing device, and/or through interacting with a physical interface of the control unit 110 of the property monitoring system.

The monitoring server 107 can determine any of various system actions 116 in response to analyzing the data 114. For example, the monitoring server 107 may determine system actions 116 that include (a) inflating more air into the jacket 103C and (b) sending a notification to the user device 112 of the resident 101C. In some implementations, the actions 116 can also include sending an instruction to the automation controls in a home security system to adjust a setting of a connected device or appliance, sending a command to a sensor 106 to collect sensor data, sounding an alarm of the property 102, or sending an alert to a third-party, such as security personnel or emergency services.

In some implementations, the actions 116 may include sending a message to the mobile device 112 of the resident 101C and requesting a response from the resident 101C. For example, the monitoring server 107 can send a message to the mobile device 112 requesting permission to adjust the configuration of an adjustable textile 103C. The monitoring server 107 can wait until it receives an affirmative response from the resident 101C (e.g., an affirmative response sent from the mobile device 112 of the resident 101C) before inflating more air to the adjustable textile 103C.

In stage (E), the monitoring server 107 performs the system actions 116. The monitoring server 107 can communicate an insulation configuration action either directly to the adjustable textile, or to another electronic device. In some implementations, the monitoring server 107 can communicate the system action to the adjustable textile 103C through the network 105. For example, the monitoring server 107 can send an insulation configuration action 104A "Removing air inside the jacket" to a jacket 101A worn by a resident 101A inside a warm sunroom of a property 102. After receiving the insulation configuration action, the jacket 103A can automatically reduce the amount of air inside the jacket.

In some implementations, the monitoring server 107 can perform the actions 116 by sending an instruction to the control unit 110 over the long-range data link. In some implementations, the monitoring server 107 can send a notification and/or alert to the mobile device 112 of the resident 101C. The monitoring server 107 can communicate with the mobile device 112 through a cellular telephony or wireless data network, through a WAN or LAN, through Wi-Fi, or through another wired or wireless communication link. The notification can be, for example, an SMS text message, an e-mail, a message displayed by an application executing on the mobile device 112, or another notification or message sent to the device 112.

In the example of FIG. 1, the monitoring server 107 performs the actions 116 by sending a notification 104A "ALERT: Low Temperature detected! Inflate the jacket more!" to a mobile device 112 of a resident 101C wearing a jacket 103C. After viewing the message on his/her mobile device, the resident 101C may determine to manually inflate the jacket 103C as needed.

In some implementations, the monitoring server 107 includes one or more machine learning modules to analyze the data 114, generate the rules 161, generate the thresholds 162, and/or determine the actions 116. For example, the monitoring server 107 can include one or more neural networks, linear or logistic regression models, decision trees, support vector machines, Bayesian techniques, nearest-neighbor or clustering techniques, or other machine learning approaches. The machine learning modules of monitoring server 107 may support supervised and/or unsupervised learning.

Though the system and method of FIG. 1 is described in the context of a jacket that can be configured to adjust inflation level, it could be similarly applied to other textiles, such as blankets, sweaters, pants, gloves, hats, shoes, sleeping bags or another textile with adjustable inflation level.

Though described above as being performed by a particular component of system 100 (e.g., the control unit 110 or the monitoring server 107), any of the various control, processing, and analysis operations can be performed by either the control unit 110, the monitoring server 107, or another computer system of the system 100. For example, the control unit 110, the monitoring server 107, or another computer system can analyze the temperature data, image data, sensor data, and other data 114 to determine the actions 116. Similarly, the control unit 110, the monitoring server 107, or another computer system can control the temperature sensors 120, 122 and 124, the camera 126, and/or other sensors 106 to collect data or control device operation.

FIGS. 2A-2C are diagrams illustrating examples 200a, 200b and 200c, respectively, of using adjustable textiles in various situations. The examples 200a, 200b and 200c can be performed, for example, by system 100. The system includes a control unit in the home that collects data from various sensors of the system. In some examples, the control unit also receives data from a user device (e.g., a smart phone or other computing device). The control unit sends the data to a monitoring server that analyzes the data and, based on the analysis, determines whether to perform one or more actions related to the textile, such as a jacket. In some implementations, the user device, the sensor, and/or the textile includes computing capability to process the data and determine whether to perform the one or more actions.

In example 200a of FIG. 2A, a user 202a wears a jacket 214a with an adjustable insulative capacity. The user 202a is playing a basketball 204 in an outdoor environment. The user 202a wears a wearable device, e.g., a smart watch 206a that can monitor activity, e.g., movement level, heart rate, etc., of the user. In some implementations, a wearable device can measure body moisture level that can indicate whether the user is sweating. The sensors of the system can measure an outdoor temperature of the environment. In some implementations, the sensors of the system can measure light conditions, e.g., amount of sunlight in an outdoor environment. The control unit collects data 208a from temperature sensors and smart watch 206a. The data 208a indicates that (i) the outdoor temperature is 35° F.; (ii) the user's heart rate is 100 beats per minute (bpm); (iii) the user's movement level is 150 steps per minute; and (iv) the current inflation level of the jacket 214a is 90%.

The control unit sends the data 208a to the monitoring server, which analyzes the data 208a to determine that the user is moving actively in a relatively cold environment. Although the jacket 214a has a high inflation level of 90% due to the relatively cold weather, the user 202a who is actively moving may prefer a lighter jacket. The monitoring server performs the actions 210a, which include deflating the jacket 214a to an inflation level of 30%, e.g., a lighter or thinner jacket. After receiving the insulation configuration action, the jacket 214a can automatically reduce the amount of air inside the jacket. In some implementations, the monitoring server can perform the actions 210a, which can include sending notification of the desired inflation level to a mobile device 212a of the user 202a. After viewing the message on the mobile device 212a, the user 202a may determine to manually deflate the jacket 214a as needed. In some implementations, the user 202a may not comply with the notification received at the mobile device 212a. For example, the user 202a may choose not manually deflate the jacket 214a. Then the system can learn the user's preference, e.g., to be warmer. Based on the learned user preference, the system can adjust its recommendations or actions 210a in the future.

The wearable device, e.g. the smart watch 206a continues to collect the user's activity level and heart rate, and sends the collected data to the control unit and/or monitoring system for further analysis. Once determined that the user 202a has stopped high intensity movement, e.g., the user stops playing basketball, the system can increase the inflation level of the jacket 214a to keep the user warm.

In example 200b of FIG. 2B, a user 202b wears a blanket 220a with an adjustable insulative capacity while sleeping in a bedroom. A motion sensor 222 installed on the bed can track sleep time and number of times the user gets out of bed. A wearable device 206b can track breathing patterns, heart rate and sleep time of the user. Audio detection devices 224 in the bedroom can track the user's snoring patterns. The control unit collects data 208b from a temperature sensor of the room, motion sensor 222, wearable device 206b, and audio device 224. The data 208b indicates that (i) the bedroom temperature is 65° F.; (ii) the user has slept 6.5 hours; and (iii) on average, the user sleeps 7 hours.

The control unit sends the data 208b to the monitoring server, which analyzes the data 208b to determine that the user is likely to wake up in 30 minutes. Although the blanket 220a is currently insulated at a comfortable level for a sleeping user under the measured room temperature, a heavier, or thicker, blanket 220b with more insulation than the current insulation level could gradually increase the user's body temperature to simulate a natural waking up experience. This is because a heavier, or thicker, blanket may provide more warmth and comfort to the user 202b when the user wakes up. The monitoring server performs the actions 210b, which include inflating the blanket 220a. After receiving the insulation configuration action, the blanket 220a can automatically increase the amount of air inside the blanket, resulting in a heavier, or thicker, blanket 220b.

In some implementations, data from other smart home sensors can be collected indicating a broad population's sleep patterns. Data for user 202b and data for population's sleep patterns can feed into an analytics engine of the monitoring system. The analytics engine of the monitoring system can benefit from the data that captures blanket thickness or weight that each sleeper uses. The monitoring system can optimize the insulation profile of the blanket 220a to achieve the most restful sleep for the user 202b.

In some implementations, when a user purchases a new blanket 220a, the system can alter insulation levels of the blanket 220a throughout an initial period of time, e.g., the first week after the user purchases the blanket. During this initial period of time, the system can track the sleep quality of the user. After the initial period of time, e.g., the first week, the system can choose a permanent insulation profile of the blanket 220a based on feedback from the user. For example, the system can provide a few different settings of the insulation levels, ask the user how his/her sleep was compared to other nights, and determine an appropriate insulation level for the user. The permanent insulation profile can include a predetermined insulation level of the blanket throughout the sleeping period. For example, the insulation level of the blanket can be higher when the user is preparing to fall asleep, lower during sleep, and higher when the user is waking up.

In some implementations, the system can determine the sleep quality of the user and calibrate the insulation level by analyzing one or more images or videos captured by one or more camera sensors. The system can determine sleep quality of the user by determining whether the user is performing certain actions during his/her sleep. For example, if the user kicked the blanket off the bed, the system can determine that the user was likely too warm and the blanket needed to be less insulated.

In general and during the initial period of time, e.g., "calibration" phase, the system can actively send notifications to the user throughout the day and can ask the user to rate his/her current comfort level. The preference of insulation level can be adjusted based on the user's rating of the current comfort level. For example, the system can ask the user to rate his/her current comfort level on a scale 1-10 from "too hot" to "too cold".

In some implementations, the blanket 220 can be configured with sensors that can collect sensor data indicateing that a user's body temperature is rising and/or sensor data that can track the movement of the user's body during sleep. Based on analysis of the sensors data, the monitoring system can determine that the user is waking up. The monitoring system can perform actions to control one or more other devices in the bedroom or the house. For example, the monitoring system can preemptively turn on the lights of the bedroom to aid the user's transition from sleeping to being awake and to provide a natural way of waking up. For example, the system can preemptively adjust the bedroom's thermostats to aid the user's transition from sleeping to being awake and to ease the user from being under a warm blanket to the cold air.

In example 200c of FIG. 2C, a first user 230 and a second user 232 share a blanket 234 with an adjustable insulative capacity. The blanket 234 contains zones to independently adjust the insulative capacity when multiple individuals share the blanket. For example, the left half of the blanket 236 and the right half of the blanket 238 can be independently inflated or deflated. The blanket includes an array of micro-sensors 241, 242, 243, 244, 245, 246, 247, 248, 249, 250, 251 and 252 that can measure and track the temperature and/or moisture condition for different parts of the blanket. For example, micro-sensors 241, 242, 243, 244, 245, and 246 can measure the body temperature for the first user 230, and micro-sensors 247, 248, 249, 250, 251, and 252 can measure the body temperature for the second user 232. The control unit collects data 208c from the array of micro-sensors 241, 242, 243, 244, 245, 246, 247, 248, 249, 250, 251 and 252. The data 208c indicates that (i) the measured body temperatures of the first user 230 from micro-sensors 241, 242, 243, 244, 245, and 246 are higher than desired; (ii) the measured body temperatures of the second user 232 from micro-sensors 247, 248, 249, 250, 251, and 252 are lower than desired.

The control unit sends the data 208c to the monitoring server, which analyzes the data 208c to determine that the first user 230 may feel too hot and may be sweating, and the second user 232 may feel cold. The monitoring server performs the actions 210c, which include (i) inflating the left part 238 of the blanket; and (ii) deflating the right part 236 of the blanket. After receiving the insulation configuration action, the blanket 234 can automatically and independently adjust the inflation level of the left part 236 of the blanket and the inflation level of the right part 238 of the blanket. This results in blanket 234a, which is the same blanket 234 with more insulation on the left and less insulation on the right, providing a comfortable level of heat protection for both users 230 and 232.

In some implementations, the first user 230 and the second user 232 may prefer different levels of warmth from the blanket 234 that they share. One or both of the users may send instructions from their mobile device 212c to the monitoring server to independently adjust the inflation configuration of a certain zone of the blanket. The monitoring server can take actions upon receiving the instruction. In some implementations, one or both of the users may use a manual pump to adjust the inflation level of a desired zone of the blanket.

In some implementations, data from micro-sensors 241, 242, 243, 244, 245, 246, 247, 248, 249, 250, 251 and 252 can be collected indicating a sleeping position of a user 230. For example, the data measuring thermodynamic outputs from micro-sensors can indicate whether the person is sleeping on the back, on the side, or on the stomach. One or more zones of the blanket can be independently adjusted according to the sleeping position of the user.

In some implementations, data from micro-sensors 241, 242, 243, 244, 245, 246, 247, 248, 249, 250, 251 and 252 can be collected indicating the distribution of the blanket. For example, the data measuring thermodynamic outputs from micro-sensors can indicate whether the blanket is tucked in under something like a mattress or a person, or is not tucked in under something like a mattress or a person. The heat under the blanket can be better retained if the blanket is tucked in than if the blanket is not tucked in. The different zones of the blanket can be independently adjusted according to the distribution of the blanket. For example, the edges of the blanket that are tucked in may not receive any air or less air than the portions of the blanket that are not tucked in.

Figure 3A:
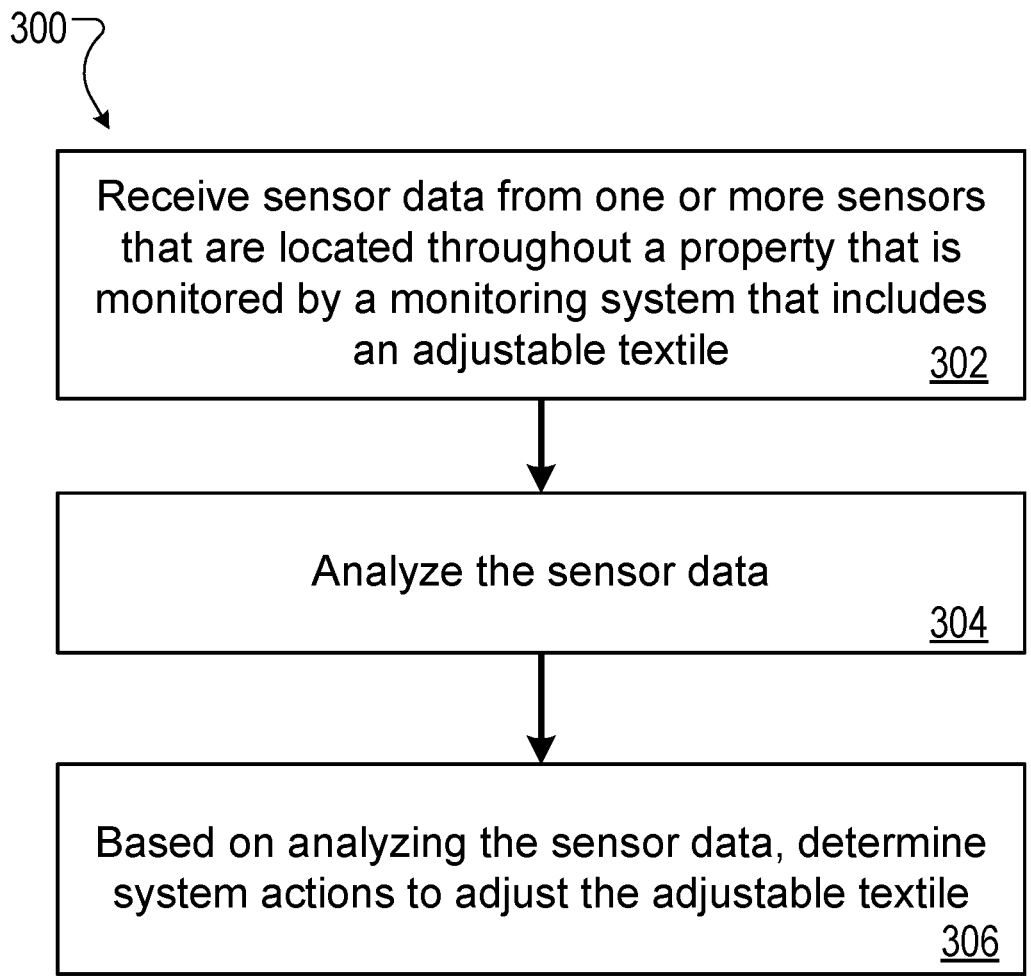
FIG. 3A is a flow chart illustrating an example of a method 300 for using an adjustable textile based on sensor data.

FIG. 3A is a flow chart illustrating an example of a method 300 for using an adjustable textile based on sensor data. Method 300 can be performed by one or more computer systems, for example, the monitoring server 107 of system 100. In some implementations, some or all of the methods can be performed by the control unit 110 of the system 100, or by another computer system located at the monitored property. Briefly, method 300 includes receiving sensor data from one or more sensors that are located throughout a property that is monitored by a monitoring system that includes an adjustable textile (302); analyzing the sensor data (304); based on analyzing the sensor data, determining system actions to adjust the adjustable textile (306).

In more detail, the monitoring server 107 or another computer system receives, from one or more sensors of a property, sensor data (302). The property is monitored by a monitoring system that includes an adjustable textile. The adjustable textile, e.g., a blanket, can be configured to adjust the amount of insulation materials in one or more layers of base materials. The sensor data can be, for example, temperature data, image, video, motion data or other types of data measured by sensors. In some implementations, the monitoring server 107 is remote from the property and a control unit 110 located at the property sends the sensor data to the monitoring server 107 over a long-range data link. The sensor data can include data related to temperature measured by a temperature sensor from various regions of an area of the property. In some implementations, the server receives a current insulation configuration of the adjustable textile.

In some implementations, the monitoring server or other computer system can obtain temperature data from sources other than one or more temperature sensors. For example, the monitoring server or other computer system can pull weather forecast data and/or historical average temperature data for the location the user is in. The monitoring server or other computer system can further process the obtained temperature data in combination with or without the sensor data received from one or more sensors.

The monitoring server or other computer system analyzes the sensor data (304). For instance, the server can process the sensor data to determine that a person wearing the adjustable textile, e.g., a jacket, has moved to a warmer room of the property. In some examples, the server may identify one or more objects, or people captured by the thermal image. In some examples, the server may perform facial recognition or object classification to identify a user of the adjustable textile. The server may also analyze the sensor data to determine an activity level of a user wearing an adjustable textile. In some examples, the server may use historic behavior patterns of a user or a population to predict insulation configuration preferences of the adjustable textile. In some implementations, the server can analyze the temperature of various zones of adjustable textile measured by an array of micro-sensors in the adjustable textile.

In some implementations, the server may analyze the sensor data along with other data provided by the monitoring system of the property. For example, the server may analyze sensor data in conjunction with other data collected by a wearable device of the user who wears the adjustable textile, or with other monitoring system data, such as a predicted behavior of a population. In some implementations, the server may include one or more machine learning modules that analyze the sensor data and/or other data (e.g., sensor data or monitoring system data).

Based on analyzing the sensor data, the monitoring server or other computer system determines one or more actions to adjust the adjustable textile (306). The action can include inflation configuration instruction to the adjustable textile, such as inflating or deflating the textile with air. For example, the server may determine an action to inflate a jacket with more air because the person who walked outside of the property may need a heavier, or thicker, jacket. For example, the server may determine an action to deflate a jacket because sensor data indicates the user is actively moving, e.g., playing basketball.

The monitoring server can also send a message to a mobile device of a user or resident, for example, a text message, an e-mail message, a push notification, a message through a software application, or another alert. For example, the server can determine an action to send a notification to a user device to alert the user to inflate the jacket with more air. In some implementations, the server may send a message to the mobile device of a user requesting permission to perform an action to the adjustable textile. For example, the server may request permission to adjust the insulation configuration setting of a jacket the user is wearing. In some cases, the server may send a message to a third-party, such as security or emergency-services personnel. For example, the server may send insulation information of a jacket to a relative of an elderly user who wears the jacket, and the relative can monitor and/or adjust the insulation level of the jacket to make sure the elderly user is comfortable. As another example, when a jacket is stolen by a stranger, the server may observe unusual behavior of the jacket or the location of the jacket, and the server can send the current location of the jacket to the owner of the jacket.

In some implementations, the adjustable textile can contain zones to independently adjust the insulative capacity when multiple users share the textile. The server can determine to adjust insulation of a portion of the adjustable textile (e.g., only inflating the left part of a blanket). The server can determine to adjust different zones of the textile independently (e.g., inflate one zone more than another zone).

The monitoring server can include a rules engine, which determines the actions based on one or more rules. The rules can be default rules, set in advance by a system administrator. In some implementations, the rules include one or more thresholds, where a threshold can relate to the detected temperature of a particular area in the property. In some implementations, the threshold can be adjusted by a user. For example, a resident of the property can set a value for a threshold temperature or time through an application on a personal mobile or non-mobile computing device. The threshold can be stored by a memory system of the server and accessed by the server. In some implementations, the server can include one or more machine learning modules to analyze the data, generate the rules, generate the thresholds, and/or determine the actions.

Figure 3B:
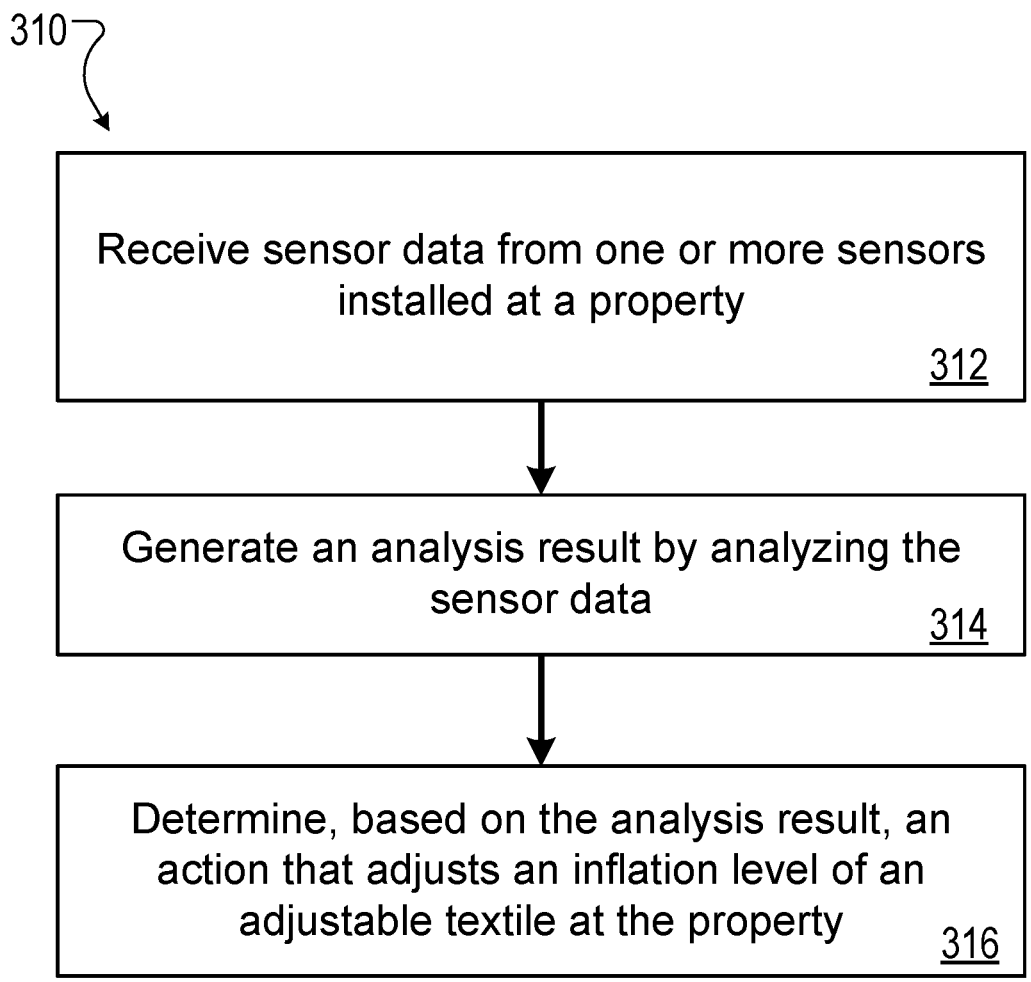
FIG. 3B is a flow chart illustrating an example of a method 310 for using an adjustable textile based on sensor data.

FIG. 3B is a flow chart illustrating an example of a method 310 for using an adjustable textile based on sensor data. Method 310 can be performed by one or more computer systems, for example, the monitoring server 107 of system 100. In some implementations, some or all of the methods can be performed by the control unit 110 of the system 100, or by another computer system located at the monitored property.

The monitoring server 107 or another computer system receives sensor data from one or more sensors installed at a property (312). The property can include indoor, or outdoor area, and can be, for example, a house, an apartment, a shed, an office, a library, a hospital, and so on. An adjustable textile is located at the property. The adjustable textile can include at least one of a clothing, a sleeping bag, or a blanket, etc., worn by a resident of the property. The adjustable textile is configurable with various levels of insulation. The one or more sensors can include at least one of a temperature sensor, a motion detector, or a camera sensor, etc. For example, the monitoring server 107 can receive sensor data captured by the temperature sensors 120, 122, and 124. For example, a door lock sensor may collect data indicating that a door from the living room to the outside is open. This can trigger a camera 126 to capture an image or video of around the door. In some implementations, the control unit 110 can send various sensor data 114 to a monitoring server 107.

The monitoring server or other computer system generates an analysis result by analyzing the sensor data (314). In some implementations, the system can determine that a user wearing the adjustable textile, e.g., a jacket, has moved from a first location to a second location. For example, the control unit 110 can receive temperature data from a fixed outside thermometer 124 that measures the outside temperature. The control unit 110 can receive temperature data from a fixed inside thermometer 122 that measures the inside temperature. The control unit 110 or the monitoring server 107 can determine a temperature difference between the inside temperature and the outside temperature. The monitoring server 107 can generate an analysis result that specifies the temperature difference between the outside and the living room.

The monitoring server or other computer system determines, based on the analysis result, an action that adjusts an inflation level of an adjustable textile at the property (316). In some implementations, the adjustable textile 101A can adjust the adjustable textile based on the action.

In some implementations, the analysis result can include temperature difference as the user moves from a first location to a second location. For example, the monitoring server 107 can determine, based on the temperature difference, that the temperature decreases when the user wearing the adjustable textile moves from the first location to the second location, e.g., from the living room to outside during cold winter season. The monitoring server 107 can determine from data 114 that the outdoor environment with temperature measured at 55° F. is colder than the living room with temperature measured at 70° F. The monitoring server 107 can determine an action 116 that increases the inflation level of the adjustable jacket 103C to keep the user 101B warm.

As another example, the monitoring server 107 can determine, based on the temperature difference measured in sensor data 114, that a temperature increases when the user wearing the adjustable textile moves from the first location to the second location, e.g., from a living room to a warmer sunroom. The monitoring server 107 can determine an action 104A that decreases the inflation level of the adjustable jacket 103A.

In some implementations, the sensor data can include sleep information 208b of a user 202b wearing an adjustable textile, e.g., an inflatable blanket 220a. The sensor data can indicate that the user is currently sleeping and has slept 6.5 hours. The sensor data further indicates that the user usually sleeps 7 hours on average. The monitoring server 107 can determine, based on sensor data 208b, that the user wearing the blanket is going to wake up. In response, the monitoring server 107 can determine an action 210b that increases the inflation level of the blanket such that the user feels warm when waking up.

In some implementations, the adjustable textile can include a first portion and a second portion, e.g., two portions of a blanket 234 shared by two users 230 and 232. The control unit 110 can obtain sensor data 208c measured from sensors 241-246 indicating user 230 feels too warm. The control unit 110 can obtain sensor data 208c measured from sensors 247-252 indicating that user 232 feels too cold. The monitoring server 107 can determine a first action 210c that adjusts a first inflation level of the first portion of the adjustable textile and a second action 210c that adjusts a second inflation level of the second portion of the adjustable textile. For example, the monitoring server 107 can determine an action that increases the inflation level of the left portion of the blanket and the monitoring server 107 can determine an action that decreases the inflation level of the right portion of the blanket.

In some implementations, the monitoring server 107 or the control unit 110 can send, to a user device 112, a notification 104c that is associated with adjusting the adjustable textile 103c. The monitoring server 107 can receive, from the user device 112, a response to the notification 104c sent by a user 101c of the user device 112. The monitoring server 107 can determine preference information of the user based on the received response. In the future, the monitoring server 107 can determine actions based on the preference information of the user. For example, the monitoring server 107 can receive updated sensor data from one or more sensors, and generates an analysis result by analyzing the updated sensor data. The monitoring server 107 can determine an action that adjusts the inflation level of the adjustable textile based on the analysis result and based on the preference information of the user.

In some implementations, the system can determine the action based on a rule that includes a threshold. For example, the monitoring server 107 can generate the rule 161 using a machine learning module, generate the threshold 162 using a machine learning module, generate the analysis result by analyzing the sensor data using a machine learning module, or determine the action using a machine learning module.

Figure 4:
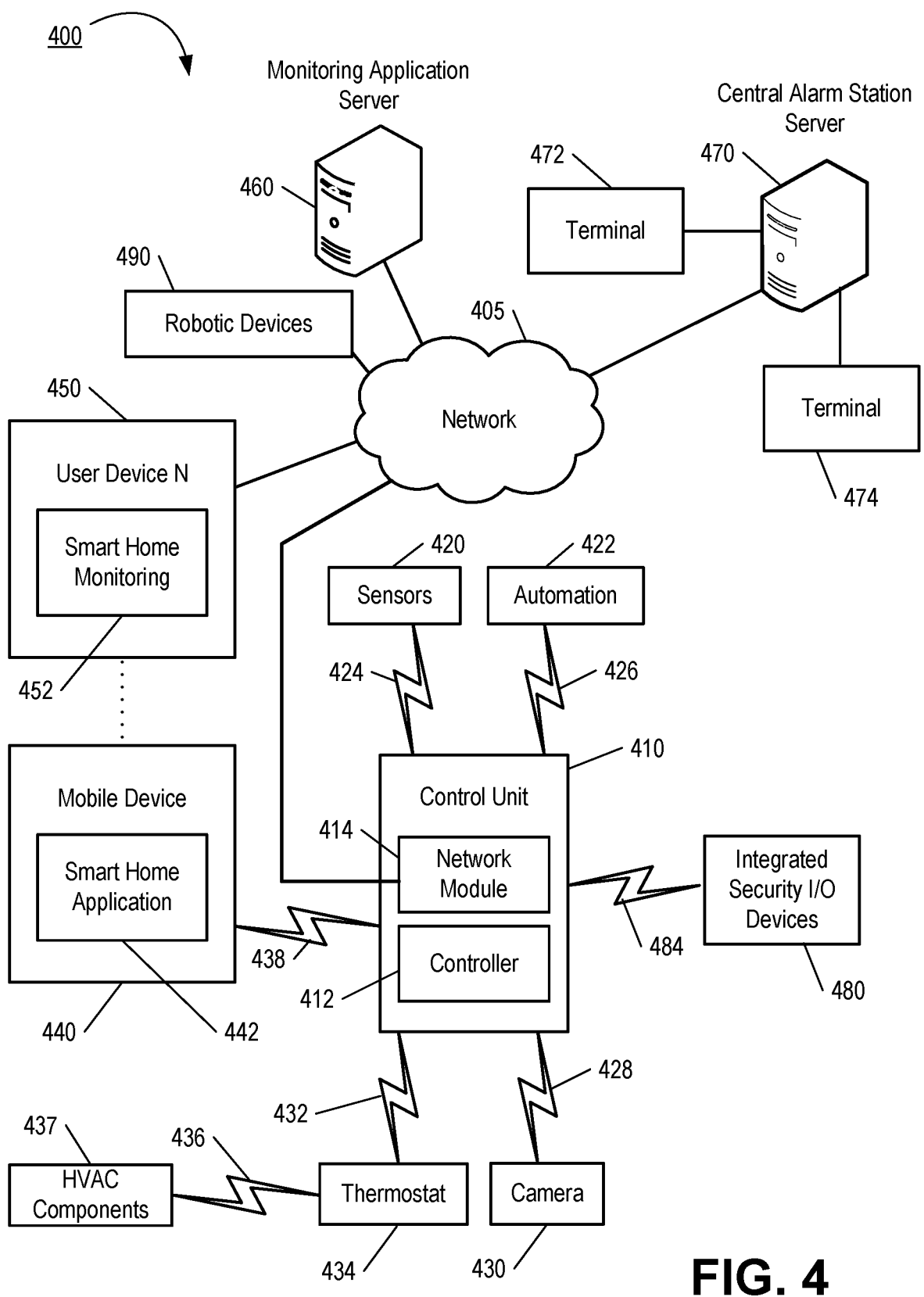
FIG. 4 is a diagram illustrating an example of a property monitoring system.

FIG. 4 is a diagram illustrating an example of a property monitoring system 400. The electronic system 400 includes a network 405, a control unit 410, one or more user devices 440 and 450, a monitoring server 460, and a central alarm station server 470. In some examples, the network 405 facilitates communications between the control unit 410, the one or more user devices 440 and 450, the monitoring server 460, and the central alarm station server 470.

The network 405 is configured to enable exchange of electronic communications between devices connected to the network 405. For example, the network 405 may be configured to enable exchange of electronic communications between the control unit 410, the one or more user devices 440 and 450, the monitoring server 460, and the central alarm station server 470. The network 405 may include, for example, one or more of the Internet, Wide Area Networks (WANs), Local Area Networks (LANs), analog or digital wired and wireless telephone networks (e.g., a public switched telephone network (PSTN), Integrated Services Digital Network (ISDN), a cellular network, and Digital Subscriber Line (DSL)), radio, television, cable, satellite, or any other delivery or tunneling mechanism for carrying data. Network 405 may include multiple networks or subnetworks, each of which may include, for example, a wired or wireless data pathway. The network 405 may include a circuit-switched network, a packet-switched data network, or any other network able to carry electronic communications (e.g., data or voice communications). For example, the network 405 may include networks based on the Internet protocol (IP), asynchronous transfer mode (ATM), the PSTN, packet-switched networks based on IP, X.25, or Frame Relay, or other comparable technologies and may support voice using, for example, VoIP, or other comparable protocols used for voice communications. The network 405 may include one or more networks that include wireless data channels and wireless voice channels. The network 405 may be a wireless network, a broadband network, or a combination of networks including a wireless network and a broadband network.

The control unit 410 includes a controller 412 and a network module 414. The controller 412 is configured to control a control unit monitoring system (e.g., a control unit system) that includes the control unit 410. In some examples, the controller 412 may include a processor or other control circuitry configured to execute instructions of a program that controls operation of a control unit system. In these examples, the controller 412 may be configured to receive input from sensors, flow meters, or other devices included in the control unit system and control operations of devices included in the household (e.g., speakers, lights, doors, etc.). For example, the controller 412 may be configured to control operation of the network module 414 included in the control unit 410.

The network module 414 is a communication device configured to exchange communications over the network 405. The network module 414 may be a wireless communication module configured to exchange wireless communications over the network 405. For example, the network module 414 may be a wireless communication device configured to exchange communications over a wireless data channel and a wireless voice channel. In this example, the network module 414 may transmit alarm data over a wireless data channel and establish a two-way voice communication session over a wireless voice channel. The wireless communication device may include one or more of a LTE module, a GSM module, a radio modem, cellular transmission module, or any type of module configured to exchange communications in one of the following formats: LTE, GSM or GPRS, CDMA, EDGE or EGPRS, EV-DO or EVDO, UMTS, or IP.

The network module 414 also may be a wired communication module configured to exchange communications over the network 405 using a wired connection. For instance, the network module 414 may be a modem, a network interface card, or another type of network interface device. The network module 414 may be an Ethernet network card configured to enable the control unit 410 to communicate over a local area network and/or the Internet. The network module 414 also may be a voice band modem configured to enable the alarm panel to communicate over the telephone lines of Plain Old Telephone Systems (POTS).

The control unit system that includes the control unit 410 includes one or more sensors. For example, the monitoring system may include multiple sensors 420. The sensors 420 may include a lock sensor, a contact sensor, a motion sensor, or any other type of sensor included in a control unit system. The sensors 420 also may include an environmental sensor, such as a temperature sensor, a water sensor, a rain sensor, a wind sensor, a light sensor, a smoke detector, a carbon monoxide detector, an air quality sensor, etc. The sensors 420 further may include a health monitoring sensor, such as a prescription bottle sensor that monitors taking of prescriptions, a blood pressure sensor, a blood sugar sensor, a bed mat configured to sense presence of liquid (e.g., bodily fluids) on the bed mat, etc. In some examples, the health-monitoring sensor can be a wearable sensor that attaches to a user in the home. The health-monitoring sensor can collect various health data, including pulse, heart rate, respiration rate, sugar or glucose level, bodily temperature, or motion data.

The sensors 420 can also include a radio-frequency identification (RFID) sensor that identifies a particular article that includes a pre-assigned RFID tag.

The control unit 410 communicates with the home automation controls 422 and a camera 430 to perform monitoring. The home automation controls 422 are connected to one or more devices that enable automation of actions in the home. For instance, the home automation controls 422 may be connected to one or more lighting systems and may be configured to control operation of the one or more lighting systems. In addition, the home automation controls 422 may be connected to one or more electronic locks at the home and may be configured to control operation of the one or more electronic locks (e.g., control Z-Wave locks using wireless communications in the Z-Wave protocol). Further, the home automation controls 422 may be connected to one or more appliances at the home and may be configured to control operation of the one or more appliances. The home automation controls 422 may include multiple modules that are each specific to the type of device being controlled in an automated manner. The home automation controls 422 may control the one or more devices based on commands received from the control unit 410. For instance, the home automation controls 422 may cause a lighting system to illuminate an area to provide a better image of the area when captured by a camera 430.

The camera 430 may be a video/photographic camera or other type of optical sensing device configured to capture images. For instance, the camera 430 may be configured to capture images of an area within a building or home monitored by the control unit 410. The camera 430 may be configured to capture single, static images of the area and also video images of the area in which multiple images of the area are captured at a relatively high frequency (e.g., thirty images per second). The camera 430 may be controlled based on commands received from the control unit 410.

The camera 430 may be triggered by several different types of techniques. For instance, a Passive Infra-Red (PIR) motion sensor may be built into the camera 430 and used to trigger the camera 430 to capture one or more images when motion is detected. The camera 430 also may include a microwave motion sensor built into the camera and used to trigger the camera 430 to capture one or more images when motion is detected. The camera 430 may have a "normally open" or "normally closed" digital input that can trigger capture of one or more images when external sensors (e.g., the sensors 420, PIR, door/window, etc.) detect motion or other events. In some implementations, the camera 430 receives a command to capture an image when external devices detect motion or another potential alarm event. The camera 430 may receive the command from the controller 412 or directly from one of the sensors 420.

In some examples, the camera 430 triggers integrated or external illuminators (e.g., Infra-Red, Z-wave controlled "white" lights, lights controlled by the home automation controls 422, etc.) to improve image quality when the scene is dark. An integrated or separate light sensor may be used to determine if illumination is desired and may result in increased image quality.

The camera 430 may be programmed with any combination of time/day schedules, system "arming state", or other variables to determine whether images should be captured or not when triggers occur. The camera 430 may enter a low-power mode when not capturing images. In this case, the camera 430 may wake periodically to check for inbound messages from the controller 412. The camera 430 may be powered by internal, replaceable batteries if located remotely from the control unit 410. The camera 430 may employ a small solar cell to recharge the battery when light is available. Alternatively, the camera 430 may be powered by the controller's 412 power supply if the camera 430 is co-located with the controller 412.

In some implementations, the camera 430 communicates directly with the monitoring server 460 over the Internet. In these implementations, image data captured by the camera 430 does not pass through the control unit 410 and the camera 430 receives commands related to operation from the monitoring server 460.

The system 400 also includes thermostat 434 to perform dynamic environmental control at the home. The thermostat 434 is configured to monitor temperature and/or energy consumption of an HVAC system associated with the thermostat 434, and is further configured to provide control of environmental (e.g., temperature) settings. In some implementations, the thermostat 434 can additionally or alternatively receive data relating to activity at a home and/or environmental data at a home, e.g., at various locations indoors and outdoors at the home. The thermostat 434 can directly measure energy consumption of the HVAC system associated with the thermostat, or can estimate energy consumption of the HVAC system associated with the thermostat 434, for example, based on detected usage of one or more components of the HVAC system associated with the thermostat 434. The thermostat 434 can communicate temperature and/or energy monitoring information to or from the control unit 410 and can control the environmental (e.g., temperature) settings based on commands received from the control unit 410.

In some implementations, the thermostat 434 is a dynamically programmable thermostat and can be integrated with the control unit 410. For example, the dynamically programmable thermostat 434 can include the control unit 410, e.g., as an internal component to the dynamically programmable thermostat 434. In addition, the control unit 410 can be a gateway device that communicates with the dynamically programmable thermostat 434. In some implementations, the thermostat 434 is controlled via one or more home automation controls 422.

A module 437 is connected to one or more components of an HVAC system associated with a home, and is configured to control operation of the one or more components of the HVAC system. In some implementations, the module 437 is also configured to monitor energy consumption of the HVAC system components, for example, by directly measuring the energy consumption of the HVAC system components or by estimating the energy usage of the one or more HVAC system components based on detecting usage of components of the HVAC system. The module 437 can communicate energy monitoring information and the state of the HVAC system components to the thermostat 434 and can control the one or more components of the HVAC system based on commands received from the thermostat 434.

In some examples, the system 400 further includes one or more robotic devices 490. The robotic devices 490 may be any type of robots that are capable of moving and taking actions that assist in home monitoring. For example, the robotic devices 490 may include drones that are capable of moving throughout a home based on automated control technology and/or user input control provided by a user. In this example, the drones may be able to fly, roll, walk, or otherwise move about the home. The drones may include helicopter type devices (e.g., quad copters), rolling helicopter type devices (e.g., roller copter devices that can fly and roll along the ground, walls, or ceiling) and land vehicle type devices (e.g., automated cars that drive around a home). In some cases, the robotic devices 490 may be devices that are intended for other purposes and merely associated with the system 400 for use in appropriate circumstances. For instance, a robotic vacuum cleaner device may be associated with the monitoring system 400 as one of the robotic devices 490 and may be controlled to take action responsive to monitoring system events.

In some examples, the robotic devices 490 automatically navigate within a home. In these examples, the robotic devices 490 include sensors and control processors that guide movement of the robotic devices 490 within the home. For instance, the robotic devices 490 may navigate within the home using one or more cameras, one or more proximity sensors, one or more gyroscopes, one or more accelerometers, one or more magnetometers, a global positioning system (GPS) unit, an altimeter, one or more sonar or laser sensors, and/or any other types of sensors that aid in navigation about a space. The robotic devices 490 may include control processors that process output from the various sensors and control the robotic devices 490 to move along a path that reaches the desired destination and avoids obstacles. In this regard, the control processors detect walls or other obstacles in the home and guide movement of the robotic devices 490 in a manner that avoids the walls and other obstacles.

In addition, the robotic devices 490 may store data that describes attributes of the home. For instance, the robotic devices 490 may store a floorplan and/or a three-dimensional model of the home that enables the robotic devices 490 to navigate the home. During initial configuration, the robotic devices 490 may receive the data describing attributes of the home, determine a frame of reference to the data (e.g., a home or reference location in the home), and navigate the home based on the frame of reference and the data describing attributes of the home. Further, initial configuration of the robotic devices 490 also may include learning of one or more navigation patterns in which a user provides input to control the robotic devices 490 to perform a specific navigation action (e.g., fly to an upstairs bedroom and spin around while capturing video and then return to a home charging base). In this regard, the robotic devices 490 may learn and store the navigation patterns such that the robotic devices 490 may automatically repeat the specific navigation actions upon a later request.

In some examples, the robotic devices 490 may include data capture and recording devices. In these examples, the robotic devices 490 may include one or more cameras, one or more motion sensors, one or more microphones, one or more biometric data collection tools, one or more temperature sensors, one or more humidity sensors, one or more air flow sensors, and/or any other types of sensors that may be useful in capturing monitoring data related to the home and users in the home. The one or more biometric data collection tools may be configured to collect biometric samples of a person in the home with or without contact of the person. For instance, the biometric data collection tools may include a fingerprint scanner, a hair sample collection tool, a skin cell collection tool, and/or any other tool that allows the robotic devices 490 to take and store a biometric sample that can be used to identify the person (e.g., a biometric sample with DNA that can be used for DNA testing).

In some implementations, the robotic devices 490 may include output devices. In these implementations, the robotic devices 490 may include one or more displays, one or more speakers, and/or any type of output devices that allow the robotic devices 490 to communicate information to a nearby user.

The robotic devices 490 also may include a communication module that enables the robotic devices 490 to communicate with the control unit 410, each other, and/or other devices. The communication module may be a wireless communication module that allows the robotic devices 490 to communicate wirelessly. For instance, the communication module may be a Wi-Fi module that enables the robotic devices 490 to communicate over a local wireless network at the home. The communication module further may be a 900 MHz wireless communication module that enables the robotic devices 490 to communicate directly with the control unit 410. Other types of short-range wireless communication protocols, such as Bluetooth, Bluetooth LE, Z-wave, Zigbee, etc., may be used to allow the robotic devices 490 to communicate with other devices in the home. In some implementations, the robotic devices 490 may communicate with each other or with other devices of the system 400 through the network 405.

The robotic devices 490 further may include processor and storage capabilities. The robotic devices 490 may include any suitable processing devices that enable the robotic devices 490 to operate applications and perform the actions described throughout this disclosure. In addition, the robotic devices 490 may include solid-state electronic storage that enables the robotic devices 490 to store applications, configuration data, collected sensor data, and/or any other type of information available to the robotic devices 490.

The robotic devices 490 are associated with one or more charging stations. The charging stations may be located at predefined home base or reference locations in the home. The robotic devices 490 may be configured to navigate to the charging stations after completion of tasks needed to be performed for the monitoring system 400. For instance, after completion of a monitoring operation or upon instruction by the control unit 410, the robotic devices 490 may be configured to automatically fly to and land on one of the charging stations. In this regard, the robotic devices 490 may automatically maintain a fully charged battery in a state in which the robotic devices 490 are ready for use by the monitoring system 400.

The charging stations may be contact based charging stations and/or wireless charging stations. For contact based charging stations, the robotic devices 490 may have readily accessible points of contact that the robotic devices 490 are capable of positioning and mating with a corresponding contact on the charging station. For instance, a helicopter type robotic device may have an electronic contact on a portion of its landing gear that rests on and mates with an electronic pad of a charging station when the helicopter type robotic device lands on the charging station. The electronic contact on the robotic device may include a cover that opens to expose the electronic contact when the robotic device is charging and closes to cover and insulate the electronic contact when the robotic device is in operation.

For wireless charging stations, the robotic devices 490 may charge through a wireless exchange of power. In these cases, the robotic devices 490 need only locate themselves closely enough to the wireless charging stations for the wireless exchange of power to occur. In this regard, the positioning needed to land at a predefined home base or reference location in the home may be less precise than with a contact based charging station. Based on the robotic devices 490 landing at a wireless charging station, the wireless charging station outputs a wireless signal that the robotic devices 490 receive and convert to a power signal that charges a battery maintained on the robotic devices 490.

In some implementations, each of the robotic devices 490 has a corresponding and assigned charging station such that the number of robotic devices 490 equals the number of charging stations. In these implementations, the robotic devices 490 always navigate to the specific charging station assigned to that robotic device. For instance, a first robotic device may always use a first charging station and a second robotic device may always use a second charging station.

In some examples, the robotic devices 490 may share charging stations. For instance, the robotic devices 490 may use one or more community charging stations that are capable of charging multiple robotic devices 490. The community charging station may be configured to charge multiple robotic devices 490 in parallel. The community charging station may be configured to charge multiple robotic devices 490 in serial such that the multiple robotic devices 490 take turns charging and, when fully charged, return to a predefined home base or reference location in the home that is not associated with a charger. The number of community charging stations may be less than the number of robotic devices 490.

In addition, the charging stations may not be assigned to specific robotic devices 490 and may be capable of charging any of the robotic devices 490. In this regard, the robotic devices 490 may use any suitable, unoccupied charging station when not in use. For instance, when one of the robotic devices 490 has completed an operation or is in need of battery charge, the control unit 410 references a stored table of the occupancy status of each charging station and instructs the robotic device to navigate to the nearest charging station that is unoccupied.

The system 400 further includes one or more integrated security devices 480. The one or more integrated security devices may include any type of device used to provide alerts based on received sensor data. For instance, the one or more control units 410 may provide one or more alerts to the one or more integrated security input/output devices 480. Additionally, the one or more control units 410 may receive one or more sensor data from the sensors 420 and determine whether to provide an alert to the one or more integrated security input/output devices 480.

The sensors 420, the home automation controls 422, the camera 430, the thermostat 434, and the integrated security devices 480 may communicate with the controller 412 over communication links 424, 426, 428, 432, 438, and 484. The communication links 424, 426, 428, 432, 438, and 484 may be a wired or wireless data pathway configured to transmit signals from the sensors 420, the home automation controls 422, the camera 430, the thermostat 434, and the integrated security devices 480 to the controller 412. The sensors 420, the home automation controls 422, the camera 430, the thermostat 434, and the integrated security devices 480 may continuously transmit sensed values to the controller 412, periodically transmit sensed values to the controller 412, or transmit sensed values to the controller 412 in response to a change in a sensed value.

The communication links 424, 426, 428, 432, 438, and 484 may include a local network. The sensors 420, the home automation controls 422, the camera 430, the thermostat 434, and the integrated security devices 480, and the controller 412 may exchange data and commands over the local network. The local network may include 802.11 "Wi-Fi" wireless Ethernet (e.g., using low-power Wi-Fi chipsets), Z-Wave, Zigbee, Bluetooth, "Homeplug" or other "Powerline" networks that operate over AC wiring, and a Category 5 (CAT5) or Category 6 (CAT6) wired Ethernet network. The local network may be a mesh network constructed based on the devices connected to the mesh network.

The monitoring server 460 is an electronic device configured to provide monitoring services by exchanging electronic communications with the control unit 410, the one or more user devices 440 and 450, and the central alarm station server 470 over the network 405. For example, the monitoring server 460 may be configured to monitor events (e.g., alarm events) generated by the control unit 410. In this example, the monitoring server 460 may exchange electronic communications with the network module 414 included in the control unit 410 to receive information regarding events (e.g., alerts) detected by the control unit 410. The monitoring server 460 also may receive information regarding events (e.g., alerts) from the one or more user devices 440 and 450.

In some examples, the monitoring server 460 may route alert data received from the network module 414 or the one or more user devices 440 and 450 to the central alarm station server 470. For example, the monitoring server 460 may transmit the alert data to the central alarm station server 470 over the network 405.

The monitoring server 460 may store sensor and image data received from the monitoring system and perform analysis of sensor and image data received from the monitoring system. Based on the analysis, the monitoring server 460 may communicate with and control aspects of the control unit 410 or the one or more user devices 440 and 450.

The monitoring server 460 may provide various monitoring services to the system 400. For example, the monitoring server 460 may analyze the sensor, image, and other data to determine an activity pattern of a resident of the home monitored by the system 400. In some implementations, the monitoring server 460 may analyze the data for temperature conditions or may determine and perform actions at the property by issuing commands to one or more of the adjustable textiles, possibly through the control unit 410.

The central alarm station server 470 is an electronic device configured to provide alarm monitoring service by exchanging communications with the control unit 410, the one or more mobile devices 440 and 450, and the monitoring server 460 over the network 405. For example, the central alarm station server 470 may be configured to monitor alerting events generated by the control unit 410. In this example, the central alarm station server 470 may exchange communications with the network module 414 included in the control unit 410 to receive information regarding alerting events detected by the control unit 410. The central alarm station server 470 also may receive information regarding alerting events from the one or more mobile devices 440 and 450 and/or the monitoring server 460.

The central alarm station server 470 is connected to multiple terminals 472 and 474. The terminals 472 and 474 may be used by operators to process alerting events. For example, the central alarm station server 470 may route alerting data to the terminals 472 and 474 to enable an operator to process the alerting data. The terminals 472 and 474 may include general-purpose computers (e.g., desktop personal computers, workstations, or laptop computers) that are configured to receive alerting data from a server in the central alarm station server 470 and render a display of information based on the alerting data. For instance, the controller 412 may control the network module 414 to transmit, to the central alarm station server 470, alerting data indicating that a sensor 420 detected motion from a motion sensor via the sensors 420. The central alarm station server 470 may receive the alerting data and route the alerting data to the terminal 472 for processing by an operator associated with the terminal 472. The terminal 472 may render a display to the operator that includes information associated with the alerting event (e.g., the lock sensor data, the motion sensor data, the contact sensor data, etc.) and the operator may handle the alerting event based on the displayed information.

In some implementations, the terminals 472 and 474 may be mobile devices or devices designed for a specific function. Although FIG. 4 illustrates two terminals for brevity, actual implementations may include more (and, perhaps, many more) terminals.

The one or more authorized user devices 440 and 450 are devices that host and display user interfaces. For instance, the user device 440 is a mobile device that hosts or runs one or more native applications (e.g., the home monitoring application 442). The user device 440 may be a cellular phone or a non-cellular locally networked device with a display. The user device 440 may include a cell phone, a smart phone, a tablet PC, a personal digital assistant ("PDA"), or any other portable device configured to communicate over a network and display information. For example, implementations may also include Blackberry-type devices (e.g., as provided by Research in Motion), electronic organizers, iPhone-type devices (e.g., as provided by Apple), iPod devices (e.g., as provided by Apple) or other portable music players, other communication devices, and handheld or portable electronic devices for gaming, communications, and/or data organization. The user device 440 may perform functions unrelated to the monitoring system, such as placing personal telephone calls, playing music, playing video, displaying pictures, browsing the Internet, maintaining an electronic calendar, etc.

The user device 440 includes a home monitoring application 442. The home monitoring application 442 refers to a software/firmware program running on the corresponding mobile device that enables the user interface and features described throughout. The user device 440 may load or install the home monitoring application 442 based on data received over a network or data received from local media. The home monitoring application 442 runs on mobile devices platforms, such as iPhone, iPod touch, Blackberry, Google Android, Windows Mobile, etc. The home monitoring application 442 enables the user device 440 to receive and process image and sensor data from the monitoring system.

The user device 450 may be a general-purpose computer (e.g., a desktop personal computer, a workstation, or a laptop computer) that is configured to communicate with the monitoring server 460 and/or the control unit 410 over the network 405. The user device 450 may be configured to display a smart home user interface 452 that is generated by the user device 450 or generated by the monitoring server 460. For example, the user device 450 may be configured to display a user interface (e.g., a web page) provided by the monitoring server 460 that enables a user to perceive images captured by the camera 430 and/or reports related to the monitoring system. Although FIG. 4 illustrates two user devices for brevity, actual implementations may include more (and, perhaps, many more) or fewer user devices.

In some implementations, the one or more user devices 440 and 450 communicate with and receive monitoring system data from the control unit 410 using the communication link 438. For instance, the one or more user devices 440 and 450 may communicate with the control unit 410 using various local wireless protocols such as Wi-Fi, Bluetooth, Z-wave, Zigbee, HomePlug (ethernet over power line), or wired protocols such as Ethernet and USB, to connect the one or more user devices 440 and 450 to local security and automation equipment. The one or more user devices 440 and 450 may connect locally to the monitoring system and its sensors and other devices. The local connection may improve the speed of status and control communications because communicating through the network 405 with a remote server (e.g., the monitoring server 460) may be significantly slower.

Although the one or more user devices 440 and 450 are shown as communicating with the control unit 410, the one or more user devices 440 and 450 may communicate directly with the sensors and other devices controlled by the control unit 410. In some implementations, the one or more user devices 440 and 450 replace the control unit 410 and perform the functions of the control unit 410 for local monitoring and long range/offsite communication.

In other implementations, the one or more user devices 440 and 450 receive monitoring system data captured by the control unit 410 through the network 405. The one or more user devices 440, 450 may receive the data from the control unit 410 through the network 405 or the monitoring server 460 may relay data received from the control unit 410 to the one or more user devices 440 and 450 through the network 405. In this regard, the monitoring server 460 may facilitate communication between the one or more user devices 440 and 450 and the monitoring system.

In some implementations, the one or more user devices 440 and 450 may be configured to switch whether the one or more user devices 440 and 450 communicate with the control unit 410 directly (e.g., through link 438) or through the monitoring server 460 (e.g., through network 405) based on a location of the one or more user devices 440 and 450. For instance, when the one or more user devices 440 and 450 are located close to the control unit 410 and in range to communicate directly with the control unit 410, the one or more user devices 440 and 450 use direct communication. When the one or more user devices 440 and 450 are located far from the control unit 410 and not in range to communicate directly with the control unit 410, the one or more user devices 440 and 450 use communication through the monitoring server 460.

Although the one or more user devices 440 and 450 are shown as being connected to the network 405, in some implementations, the one or more user devices 440 and 450 are not connected to the network 405. In these implementations, the one or more user devices 440 and 450 communicate directly with one or more of the monitoring system components and no network (e.g., Internet) connection or reliance on remote servers is needed.

In some implementations, the one or more user devices 440 and 450 are used in conjunction with only local sensors and/or local devices in a house. In these implementations, the system 400 includes the one or more user devices 440 and 450, the sensors 420, the home automation controls 422, the camera 430, and the robotic devices 490. The one or more user devices 440 and 450 receive data directly from the sensors 420, the home automation controls 422, the camera 430, and the robotic devices 490, and sends data directly to the sensors 420, the home automation controls 422, the camera 430, and the robotic devices 490. The one or more user devices 440, 450 provide the appropriate interfaces/processing to provide visual surveillance and reporting.

In other implementations, the system 400 further includes network 405 and the sensors 420, the home automation controls 422, the camera 430, the thermostat 434, and the robotic devices 490, and are configured to communicate sensor and image data to the one or more user devices 440 and 450 over network 405 (e.g., the Internet, cellular network, etc.). In yet another implementation, the sensors 420, the home automation controls 422, the camera 430, the thermostat 434, and the robotic devices 490 (or a component, such as a bridge/router) are intelligent enough to change the communication pathway from a direct local pathway when the one or more user devices 440 and 450 are in close physical proximity to the sensors 420, the home automation controls 422, the camera 430, the thermostat 434, and the robotic devices 490 to a pathway over network 405 when the one or more user devices 440 and 450 are farther from the sensors 420, the home automation controls 422, the camera 430, the thermostat 434, and the robotic devices 490.

In some examples, the system leverages GPS information from the one or more user devices 440 and 450 to determine whether the one or more user devices 440 and 450 are close enough to the sensors 420, the home automation controls 422, the camera 430, the thermostat 434, and the robotic devices 490 to use the direct local pathway or whether the one or more user devices 440 and 450 are far enough from the sensors 420, the home automation controls 422, the camera 430, the thermostat 434, and the robotic devices 490 that the pathway over network 405 is required.

In other examples, the system leverages status communications (e.g., pinging) between the one or more user devices 440 and 450 and the sensors 420, the home automation controls 422, the camera 430, the thermostat 434, and the robotic devices 490 to determine whether communication using the direct local pathway is possible. If communication using the direct local pathway is possible, the one or more user devices 440 and 450 communicate with the sensors 420, the home automation controls 422, the camera 430, the thermostat 434, and the robotic devices 490 using the direct local pathway. If communication using the direct local pathway is not possible, the one or more user devices 440 and 450 communicate with the sensors 420, the home automation controls 422, the camera 430, the thermostat 434, and the robotic devices 490 using the pathway over network 405.

In some implementations, the system 400 provides end users with access to images captured by the camera 430 to aid in decision making. The system 400 may transmit the images captured by the camera 430 over a wireless WAN network to the user devices 440 and 450. Because transmission over a wireless WAN network may be relatively expensive, the system 400 can use several techniques to reduce costs while providing access to significant levels of useful visual information (e.g., compressing data, down-sampling data, sending data only over inexpensive LAN connections, or other techniques).

In some implementations, a state of the monitoring system and other events sensed by the monitoring system may be used to enable/disable video/image recording devices (e.g., the camera 430). In these implementations, the camera 430 may be set to capture images on a periodic basis when the alarm system is armed in an "away" state, but set not to capture images when the alarm system is armed in a "home" state or disarmed. In addition, the camera 430 may be triggered to begin capturing images when the alarm system detects an event, such as an alarm event, a door-opening event for a door that leads to an area within a field of view of the camera 430, or motion in the area within the field of view of the camera 430. In other implementations, the camera 430 may capture images continuously, but the captured images may be stored or transmitted over a network when needed.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device.

Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

The invention claimed is:

1. A computer-implemented method comprising:
receiving sensor data from one or more sensors installed at a property;
generating an analysis result by analyzing the sensor data;
determining, using the analysis result, a first adjustment for an inflation level of an adjustable textile at the property;
sending, to a device, a message that is associated with the first adjustment for the adjustable textile;
receiving, from the device, a response to the message;
determining, using the response, a second adjustment for the inflation level of the adjustable textile; and
sending, to a controller for the adjustable textile and using data for the second adjustment, an instruction to cause the controller to adjust the inflation level of the adjustable textile according to the second adjustment.

2. The method of claim 1, wherein generating the analysis result by analyzing the sensor data comprises:
determining that a user wearing the adjustable textile has moved from a first location to a second location; and
determining a temperature difference between the first location and the second location, wherein the analysis result specifies the temperature difference.

3. The method of claim 2, wherein determining, using the analysis result, the first adjustment for the inflation level of the adjustable textile comprises:
determining, using the temperature difference, that a temperature decreases when the user wearing the adjustable textile moves from the first location to the second location; and
in response, determining the first adjustment that increases the inflation level of the adjustable textile.

4. The method of claim 2, wherein determining, using the analysis result, the first adjustment for the inflation level of the adjustable textile comprises:
determining, using the temperature difference, that a temperature increases when the user wearing the adjustable textile moves from the first location to the second location; and
in response, determining the first adjustment that decreases the inflation level of the adjustable textile.

5. The method of claim 1, wherein the sensor data comprise sleep information of a user wearing the adjustable textile, and the method comprises:
determining, using the sensor data, that the user wearing the adjustable textile is waking up; and
in response, determining the first adjustment that increases the inflation level of the adjustable textile.

6. The method of claim 1, further comprising:
determining preference information of a user using the response to the message;
receiving second sensor data from the one or more sensors;
generating a second analysis result by analyzing the second sensor data; and
determining the second adjustment for the inflation level of the adjustable textile using the second analysis result and the preference information of the user.

7. The method of claim 1, wherein sending the instruction comprises adjusting the inflation level of the adjustable textile according to the second adjustment.

8. The method of claim 1, wherein determining the first adjustment comprises determining the first adjustment based on a rule that includes a threshold.

9. The method of claim 8, comprising at least one of:
generating the rule using a machine learning module;
generating the threshold using a machine learning module;
generating the analysis result by analyzing the sensor data using a machine learning module; or
determining the first adjustment using a machine learning module.

10. The method of claim 1, wherein the adjustable textile comprises a first portion and a second portion, and the method comprises:
determining, based on the analysis result, a first action that adjusts a first inflation level of the first portion of the adjustable textile; and
determining, based on the analysis result, a second action that adjusts a second inflation level of the second portion of the adjustable textile.

11. The method of claim 1, wherein the adjustable textile comprises at least one of clothing, a sleeping bag, or a blanket worn by a resident of the property, and the adjustable textile is configurable with various levels of insulation.

12. The method of claim 1, wherein the one or more sensors comprise at least one of a temperature sensor, a motion detector, or a camera sensor.

13. A system comprising:
one or more computers and one or more storage devices storing instructions that are operable, when executed by the one or more computers, to cause the one or more computers to perform operations comprising:
receiving sensor data from one or more sensors installed at a property;
generating an analysis result by analyzing the sensor data;
determining, using the analysis result, a first adjustment for an inflation level of an adjustable textile at the property;
sending, to a device, a message that is associated with the first adjustment for the adjustable textile;
receiving, from the device, a response to the message;
determining, using the response, a second adjustment for the inflation level of the adjustable textile; and
sending, to a controller for the adjustable textile and using data for the second adjustment, an instruction to cause the controller to adjust the inflation level of the adjustable textile according to the second adjustment.

14. The system of claim 13, wherein generating the analysis result by analyzing the sensor data comprises:
determining that a user wearing the adjustable textile has moved from a first location to a second location; and
determining a temperature difference between the first location and the second location, wherein the analysis result specifies the temperature difference.

15. The system of claim 14, wherein determining, using the analysis result, the first adjustment for the inflation level of the adjustable textile comprises:
determining, using the temperature difference, that a temperature decreases when the user wearing the adjustable textile moves from the first location to the second location; and
in response, determining the first adjustment that increases the inflation level of the adjustable textile.

16. The system of claim 14, wherein determining, using the analysis result, the first adjustment for the inflation level of the adjustable textile comprises:
determining, using the temperature difference, that a temperature increases when the user wearing the adjustable textile moves from the first location to the second location; and
in response, determining the first adjustment that decreases the inflation level of the adjustable textile.

17. The system of claim 13, wherein the sensor data comprise sleep information of a user wearing the adjustable textile, and the operations comprise:
determining, using the sensor data, that the user wearing the adjustable textile is waking up; and
in response, determining the first adjustment that increases the inflation level of the adjustable textile.

18. The system of claim 13, the operations further comprise:
determining preference information of a user using the response to the message;
receiving second sensor data from the one or more sensors;
generating a second analysis result by analyzing the second sensor data; and
determining the second adjustment for the inflation level of the adjustable textile using the second analysis result and the preference information of the user.

19. The system of claim 13, wherein sending the instruction comprises adjusting the inflation level of the adjustable textile according to the second adjustment.

20. A non-transitory computer-readable medium storing software comprising instructions executable by one or more computers which, upon such execution, cause the one or more computers to perform operations comprising:
receiving sensor data from one or more sensors installed at a property;
generating an analysis result by analyzing the sensor data;
determining, using the analysis result, a first adjustment for an inflation level of an adjustable textile at the property;
sending, to a device, a message that is associated with the first adjustment for the adjustable textile;
receiving, from the device, a response to the message;
determining, using the response, a second adjustment for the inflation level of the adjustable textile; and
sending, to a controller for the adjustable textile and using data for the second adjustment, an instruction to cause the controller to adjust the inflation level of the adjustable textile according to the second adjustment.

* * * * *